(12) United States Patent
Russell et al.

(10) Patent No.: US 11,832,995 B2
(45) Date of Patent: Dec. 5, 2023

(54) GRASPABLE SURGICAL DEVICE

(71) Applicant: Vascular Technology, Incorporated, Nashua, NH (US)

(72) Inventors: Ronald H. Russell, Londonderry, NH (US); Stephen Martone, Nashua, NH (US); David Regan, Pelham, NH (US); Rachana S. Suchdev, Hollis, NH (US); Trevor Jacob Laughlin, Minneapolis, MN (US); Gary Douglas, Billerica, MA (US)

(73) Assignee: Vascular Technology, Incorporated, Nashua, NH (US)

( * ) Notice: Subject to any disclaimer, the term of this patent is extended or adjusted under 35 U.S.C. 154(b) by 0 days.

(21) Appl. No.: 16/926,073

(22) Filed: Jul. 10, 2020

(65) Prior Publication Data
US 2021/0008256 A1    Jan. 14, 2021

Related U.S. Application Data

(60) Provisional application No. 62/872,476, filed on Jul. 10, 2019.

(51) Int. Cl.
*A61M 3/02* (2006.01)
*A61M 39/10* (2006.01)
(Continued)

(52) U.S. Cl.
CPC .............. *A61B 90/08* (2016.02); *A61M 1/77* (2021.05); *A61M 3/0283* (2013.01);
(Continued)

(58) Field of Classification Search
CPC ........ A61M 1/0023; A61M 1/84; A61M 1/86; A61M 1/87; A61M 3/0279; A61M 2039/1077
See application file for complete search history.

(56) References Cited

U.S. PATENT DOCUMENTS 229,521 A  *  7/1880  Clifford .................... B05B 1/12
                                                    239/480
1,882,213 A  * 10/1932  Donovan .............. A61M 5/158
                                                    27/24.1
(Continued)

FOREIGN PATENT DOCUMENTS

CN    105208962 B  *  6/2018 .............. A61B 34/30
DE       3811639 A1 * 10/1989 ........ A61M 25/0637
(Continued)

OTHER PUBLICATIONS

Matweb for ABS: https://www.matweb.com/search/DataSheet.aspx?MatGUID=eb7a78f5948d481c9493a67f0d089646 , accessed Aug. 24, 2022 (Year: 2022).*
(Continued)

*Primary Examiner* — Katherine H Schwiker
*Assistant Examiner* — Adam J. Cermak
(74) *Attorney, Agent, or Firm* — Finch & Maloney PLLC

(57) ABSTRACT

A system for adapting a tubular surgical device for grasping by a surgical instrument is provided that has a distal portion, an adaptor positioned proximally and configured to be disposed about or within a lumen of the tubular surgical device, which has an effective durometer to resist crushing by the surgical instrument. In some embodiments, the adaptor is configured with an external diameter greater than the internal diameter of the lumen of the tubular surgical device. In some embodiments, the adaptor is configured with an external diameter less than or equal to the internal diameter of the tubular surgical device.

16 Claims, 21 Drawing Sheets

(51) Int. Cl.
*A61M 1/00* (2006.01)
*A61B 90/00* (2016.01)
*A61M 39/00* (2006.01)

(52) U.S. Cl.
CPC ..... *A61M 39/00* (2013.01); *A61M 2039/1077* (2013.01); *A61M 2205/02* (2013.01)

(56) References Cited

U.S. PATENT DOCUMENTS

| | | | | |
|---|---|---|---|---|
| 2,123,889 A * | 7/1938 | Gleason | ............... | F16L 21/005 285/114 |
| 2,220,493 A * | 11/1940 | Pixler | ................... | A61B 16/00 210/239 |
| 2,290,258 A * | 7/1942 | Svet | ....................... | B05B 1/185 239/567 |
| 3,913,577 A * | 10/1975 | Nehra | ..................... | A61M 1/84 251/344 |
| 4,015,600 A * | 4/1977 | Liautaud | ........... | A61M 25/0637 604/177 |
| 4,068,664 A * | 1/1978 | Sharp | ...................... | A61M 1/84 604/268 |
| 4,324,236 A * | 4/1982 | Gordon | ............. | A61M 25/0637 128/DIG. 26 |
| 4,324,239 A * | 4/1982 | Gordon | ................ | A61M 39/26 604/122 |
| 4,490,138 A * | 12/1984 | Lipsky | ................... | A61M 1/84 604/40 |
| 4,767,404 A * | 8/1988 | Renton | .................. | A61M 1/84 604/48 |
| 4,957,488 A * | 9/1990 | Cameron | .......... | A61M 25/0637 604/161 |
| 5,171,223 A * | 12/1992 | Herzberg | ........... | A61B 1/00094 604/104 |
| 5,279,573 A * | 1/1994 | Klosterman | .... | A61M 25/09041 206/403 |
| 5,571,211 A | 11/1996 | Hiemisch et al. | | |
| 5,643,197 A * | 7/1997 | Brucker | ............. | A61B 18/1492 604/20 |
| 5,713,889 A * | 2/1998 | Chang | ................... | A61B 17/11 606/1 |
| 5,897,534 A * | 4/1999 | Heim | ...................... | A61M 1/84 604/266 |
| 6,068,477 A * | 5/2000 | Mahlmann | ............. | A61C 17/08 433/136 |
| 6,346,107 B1 * | 2/2002 | Cucin | ............... | A61B 17/32002 606/49 |
| 7,178,521 B2 * | 2/2007 | Burrow | ............ | A61M 16/0816 128/202.27 |
| 7,694,821 B1 * | 4/2010 | Asfora | ................... | A61M 1/82 206/570 |
| 7,776,004 B2 * | 8/2010 | Yarger | .................... | A61M 1/84 604/35 |
| 7,955,318 B1 * | 6/2011 | Schultz | ................... | A61M 1/87 604/319 |
| 10,709,532 B2 * | 7/2020 | Roshkovan | ........... | A61C 17/08 |
| 11,135,350 B2 * | 10/2021 | Jacovini | ................. | A61M 1/86 |
| 2002/0072712 A1 * | 6/2002 | Nool | ................. | A61M 25/0136 604/167.01 |
| 2004/0056751 A1 * | 3/2004 | Park | ......................... | A61B 8/12 337/139 |
| 2006/0100605 A1 * | 5/2006 | Bicakci | ................... | A61M 1/84 604/264 |
| 2008/0200884 A1 * | 8/2008 | Perkins | ................... | A61M 1/84 604/294 |
| 2010/0063441 A1 * | 3/2010 | Grunewald | ........ | A61B 5/02007 604/95.04 |
| 2010/0312186 A1 * | 12/2010 | Suchdev | ................ | A61B 17/32 604/131 |
| 2012/0273045 A1 * | 11/2012 | Waldman | .......... | A61M 16/0484 137/565.23 |
| 2012/0289894 A1 * | 11/2012 | Douglas | .................. | A61M 1/85 604/31 |
| 2014/0276949 A1 * | 9/2014 | Staunton | ................ | A61B 34/30 606/130 |
| 2015/0231361 A1 * | 8/2015 | O'Keefe | ........... | A61M 25/0026 604/164.13 |
| 2015/0374445 A1 * | 12/2015 | Gombert | ............. | B25J 19/0075 606/130 |
| 2017/0281905 A1 * | 10/2017 | May | .................. | A61M 25/0067 |
| 2018/0098871 A1 * | 4/2018 | Sasse | .................... | A61F 5/0076 |
| 2018/0154069 A1 * | 6/2018 | Potter | ............... | A61B 18/1492 |
| 2018/0228481 A1 * | 8/2018 | Hartoumbekis | ... | A61B 17/0218 |
| 2020/0000565 A1 * | 1/2020 | Roshkovan | ............. | A61M 1/84 |

FOREIGN PATENT DOCUMENTS

| | | | | |
|---|---|---|---|---|
| DE | 9408804 U | | 8/1994 | |
| DE | 10352296 A1 * | | 6/2005 | .......... A61M 1/0037 |
| DE | 102013002813 A1 | | 8/2014 | |
| DE | 102018115250 A1 * | | 1/2020 | .......... A61M 1/008 |
| NL | 1022778 C2 * | | 8/2004 | .......... A61M 1/008 |
| WO | WO-2013052906 A2 * | | 4/2013 | ...... A61M 25/09041 |
| WO | WO-2016044388 A1 * | | 3/2016 | ....... A61F 13/00068 |

OTHER PUBLICATIONS

International Search Report and Written Opinion recieved for PCT/US2020/041658, dated Oct. 29, 2020. 13 pages.
International Preliminary Report on Patentability received for PCT/US2020/041658, dated Jan. 20, 2022. 8 pp.

\* cited by examiner

GRASPABLE SURGICAL DEVICE

TECHNICAL FIELD

This disclosure relates to surgical instruments and more particularly, to surgical instruments configured to be grasped by another surgical device for use with suction and/or irrigation devices.

BACKGROUND

In surgical procedures, it is often necessary to irrigate sterile solutions into and/or aspirate bodily or irrigant fluids out of the surgical field. Traditionally, suction/irrigation devices have been designed to function as hand held tools intended for use by the operating surgeon or an operative assistant. These hand-held devices typically incorporate a valve mechanism which the surgeon manipulates manually to control suction and irrigation functions. A common valve configuration is known as a "trumpet valve." The trumpet valve consists of an irrigation button and a suction button, each of which can be manually depressed by the operator against a compression spring to engage a valve barrel. Manual depression of the suction button allows for aspiration through the device, while depression of the irrigation button allows for the irrigation of fluids through the device.

Recently, robot assisted surgery has been increasingly employed by surgeons to perform technically challenging procedures in a minimally invasive fashion. In robot assisted surgery, the operating surgeon sits at a robotic console and remotely controls robotic arms within the surgical field to perform the surgery. An assistant surgeon is present at the patient's side to manipulate tools that cannot be controlled robotically. One such tool is the suction/irrigation device.

Some suction/irrigation devices that are employed in robot assisted surgery are devices that were designed for laparoscopic surgery. The assistant surgeon inserts a rigid laparoscopic suction/irrigation probe through an accessory port and then manually manipulates this probe within the surgical field. As mentioned above, the control buttons on this probe consist of a dual trumpet valve which must be manually pressed and depressed by the assistant surgeon and cannot be manipulated by the lead surgeon seated at the robotic console. Thus, the lead surgeon must continuously instruct the assistant as to when, where and how to utilize the device throughout the surgical case.

SUMMARY

In a first example, a system for adapting a tubular surgical device for grasping by a surgical instrument is provided, the system comprising a grasper receiving section comprising a distal portion and a proximal portion, and an adaptor configured to be at least one of disposed within a lumen or disposed around a lumen of the tubular surgical device, wherein the adaptor is of a durometer to resist crushing of the adaptor by the surgical instrument.

Example 2 includes the subject matter of Example 1, wherein the adaptor is an overmolded portion configured to be disposed around a lumen of the tubular surgical device.

Example 3 includes the subject matter of Example 1, wherein a cross section of the distal portion is formed in a shape selected from a list comprising a pentagon, a hexagon, a heptagon, a nonagon, and a decagon.

Example 4 includes the subject matter of Example 1, wherein the distal portion, the proximal portion, and the adaptor are formed from a unitary piece of material.

Example 5 includes the subject matter of Example 1, wherein the adaptor is formed from a metal.

Example 6 includes the subject matter of Example 1, wherein the grasper receiving section is formed from a biocompatible material selected from a list comprising polyurethane, aliphatic polyamides, semialiphatic polyamides, polysulfone, and block copolymers made up of rigid polyamide blocks and soft polyether blocks (i.e. PEBAX®).

Example 7 includes the subject matter of Example 1, wherein the tubular surgical device has a smooth exterior surface.

Example 8 includes the subject matter of Example 1, wherein the tubular surgical device has a fluted exterior surface.

Example 9 includes the subject matter of Example 1, wherein the distal portion comprises one or more diversion holes.

Example 10 includes the subject matter of Example 1, wherein the durometer is a Shore durometer of between 30D and 150D.

Example 11 includes the subject matter of Example 10, wherein the durometer is a Shore durometer of between 70D and 95D.

Example 12 includes the subject matter of Example 1, and further includes one or more wings extending from the grasper receiving section.

Example 13 includes the subject matter of Example 12, wherein at least one of the distal portion and the proximal portion is provided with a textured surface to resist sliding of the grasper receiving section from between jaws of the surgical instrument.

Example 14 includes the subject matter of Example 13, wherein a coefficient of friction provided by the textured surface is between 0.04 and 0.6.

Example 15 includes the subject matter of Example 12, wherein the one or more wings are configured with an arcuate contour on an edge of at least one of a proximal and distal end of the one or more wings.

Example 16 includes the subject matter of Example 12, wherein the one or more wings are narrower proximally and extend wider distally.

Example 17 includes the subject matter of Example 1, and further includes one or more longitudinal slots positioned on the proximal portion.

Example 18 includes the subject matter of Example 1, wherein a lumen extending through the distal portion and the proximal portion comprises two or more co-extruded layers.

Example 19 includes the subject matter of Example 1, wherein a lumen extending through the distal portion and the proximal portion includes a stepdown configured to provide a wider lumen proximally and a narrower lumen distally.

Example 20 includes the subject matter of Example 1, and further includes a set of grooves positioned in the distal portion, forming a plurality of distally extending fingers.

Example 21 includes the subject matter of Example 1, wherein the adaptor is coupled to the lumen via at least one of an interference fit, adhering using an adhesive, ultrasonic welding, and being thermoformed directly into the lumen.

Example 22 includes the subject matter of Example 12, wherein the one or more wings are positioned on at least one of an overmolded portion, the distal portion, the proximal portion, the adaptor, and the tubular surgical device.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the subject matter described herein.

BRIEF DESCRIPTION OF THE DRAWINGS

The drawings described herein are for illustration purposes only and are not intended to limit the scope of the present disclosure in any way.

FIG. 17B shows an edge-on view of a curved portion of the tubing. FIG. 17C is a detail view of the circled region in FIG. 17B.

FIG. 17D is a detail view of the circled region in FIG. 17A.

FIG. 19A shows a curved portion of the tubing.

FIG. 19C is a detail view of the circled region in FIG. 19A.

FIG. 19D is a detail view of the circled region in FIG. 19B.

Figure 1:
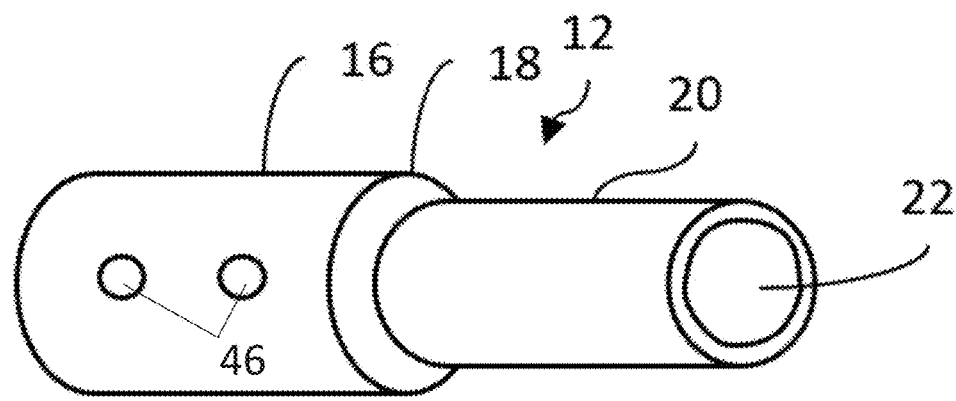
FIG. 1 illustrates a perspective view of a graspable suction tip shown from the male device adaptor end, in accordance with some embodiments of the disclosure.

These and other features of the present embodiments will be understood better by reading the following detailed description, taken together with the figures herein described. The accompanying drawings are not intended to be drawn to scale. In the drawings, each identical or nearly identical component that is illustrated in various figures may be represented by a like numeral. For purposes of clarity, not every component may be labeled in every drawing.

DETAILED DESCRIPTION

A hand-held suction/irrigation device can pose problems in the realm of robot assisted surgery, laparoscopic procedures, or open surgical procedures. In many open surgical procedures, the operating surgeon will often require an assistant to perform suction and/or irrigation within the surgical field while the surgeon is performing other surgical maneuvers (ex. suturing or dissection). In these instances, the surgeon will often have an instrument in each hand, preventing him/her from operating the valves on a traditional suction/irrigation device.

Graspers are commonly used to capture and hold tissues in a surgical locus. A surgical locus is defined herein as a region in a minimally invasive surgical field either within the patient or immediately adjacent to incisions in the patient. Typical graspers utilize two opposing metal jaws joined at a fulcrum and having knurled or otherwise textured surfaces on opposing faces. These textured surfaces are configured to provide friction which prevents the item to be grasped from sliding out of the jaws of a grasper as they are closed. As items to be grasped are typically soft, such as tissue, or small, as in suturing needles, these textures provide adequate grip. Graspers may also be used to grab and reposition a distal portion of a suction/irrigation tip, for example. Current distal portion designs pose challenges in easily slipping out of the graspers. Distal portions may slip out from the hold of a set of graspers for different reasons.

Distal portions with larger diameters and/or those made from rigid or hard material do not allow the textured surface of a grasper to grip adequately as an insufficient area of the instrument is in contact with the grasper. For distal portions of instruments including an internal lumen, too great a pressure applied by the grasper could crush or occlude the lumen. Improvements are needed for a graspable distal portion designed to be easily picked up and manipulated using surgical instruments such as graspers.

The present disclosure provides for an appropriately designed suction/irrigation device to be utilized within the surgical field which is configured to be controlled in a hands-free or remote fashion. The present disclosure provides an improved graspable portion that would allow a set of graspers to bite into the graspable portion. The present disclosure provides an improved graspable portion that is configured with less rigid, more pliable materials. The present disclosure provides an improved graspable portion that is configured with a balance of pliable and rigid materials. The present disclosure provides an improved graspable portion configured with slots or grooves. The slots or grooves can be configured to improve pliability and/or graspability.

Thus, the graspable portion is provided for interfacing at a distal end of tubing associated with a suction, irrigation, and/or insufflation system. For instruments which include an internal lumen, and particularly instruments utilized for suction, irrigation, and/or insufflation, it is critical that all components are designed to minimize occlusion and/or other blocking of the lumen. In cases when too great a pressure is applied, for example, the lumen may become crushed or occluded.

The improved graspable portion disclosed herein is a generally cylindrical section of material that is configured to be insertable into or around a distal end of tubing associated with suction, irrigation, and/or insufflation. In some embodiments, the improved graspable portion is configured to interface with a robotic surgery platform. In some embodiments, the improved graspable portion is configured to interface with tubing comprising polyvinyl chloride (PVC) or other plastic. In some embodiments, the improved graspable portion is configured to prevent occlusion of a lumen extending therethrough and extending into the tubing. In some embodiments, the improved graspable portion comprises one or more flexible wings, one or more longitudinal slots cut through the circumference, one or more tapered tabs or swept tabs, or a combination thereof. In some embodiments, the improved device may be thermoformed and/or may be provided with a tabbed tubing bond.

Swept wings, flexible wings, wings, loops, flags, grooves, and/or flutes are configured to provide extra surface area or textured surface to facilitate ease of grasping the graspable portion and moving the tip during a surgical procedure. As used herein, a graspable portion includes a grasper receiving section or a graspable suction tip. Graspable portion includes an adaptor configured for insertion into or around tubing. As used herein, adaptor is defined as the portion of the grasper receiving section configured to engage with tubing. As used herein, adaptor may include one or more of a male device adaptor, a female device adaptor, an overmolded portion, a tube, or a cylindrical portion. As used herein, adaptor includes the portion of material extending into or around tubing. In some embodiments, graspable portion includes a piece of material which can be attached to tubing. In some embodiments, graspable portion includes an overmolded portion configured to surround tubing with tubing extending therethrough. In some embodiments, graspable portion includes a portion of tubing that is specially designed for grasping.

It may be desirable to reposition the grasper receiving section or graspable suction tip to (1) provide suction, irrigation, or insufflation to a surgical region, or (2) use the tubing and graspable suction tip to move tissue out of the way of the surgical locus so that the surgeon can gain improved visualization of the surgical area.

Figure 2:
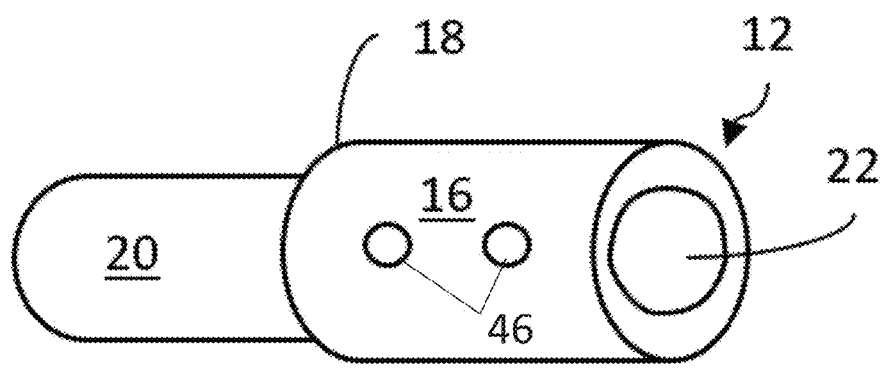
FIG. 2 illustrates a perspective view of a graspable suction tip shown from the distal portion end, in accordance with some embodiments of the disclosure.
Figure 4:
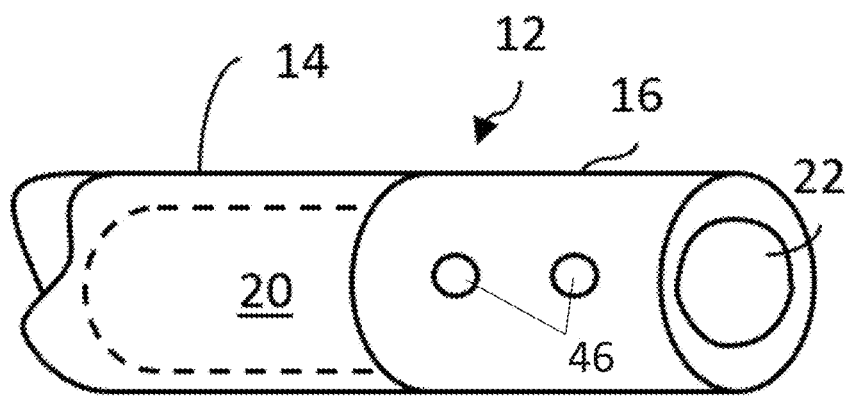
FIG. 4 illustrates a perspective view of a graspable suction tip disposed in a device, in accordance with some embodiments of the disclosure.
Figure 5:
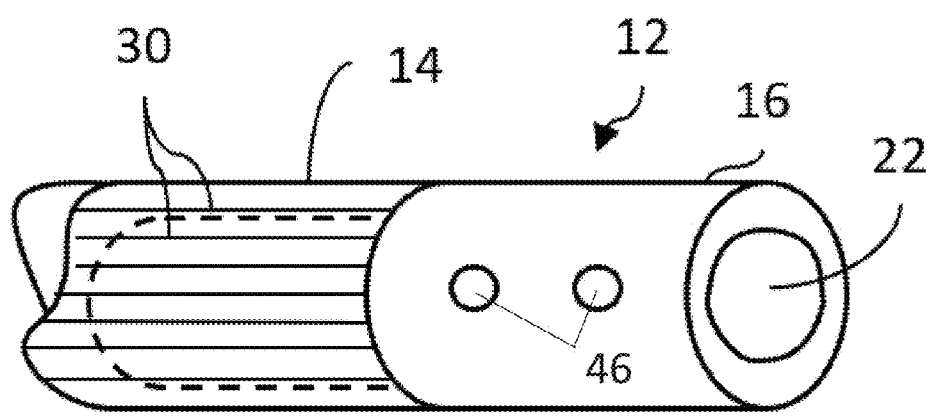
FIG. 5 illustrates a perspective view of a graspable suction tip disposed in a device, the device being provided with a fluted exterior, in accordance with some embodiments of the disclosure.
Figure 6:
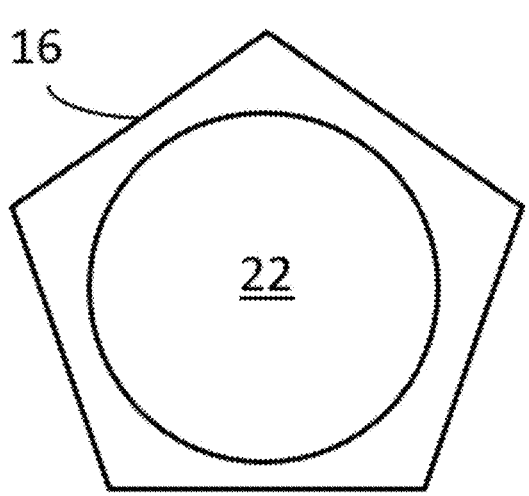
FIG. 6 illustrates an end elevation view of a graspable suction tip with a pentagonal cross section, in accordance with some embodiments of the disclosure.
Figure 7:
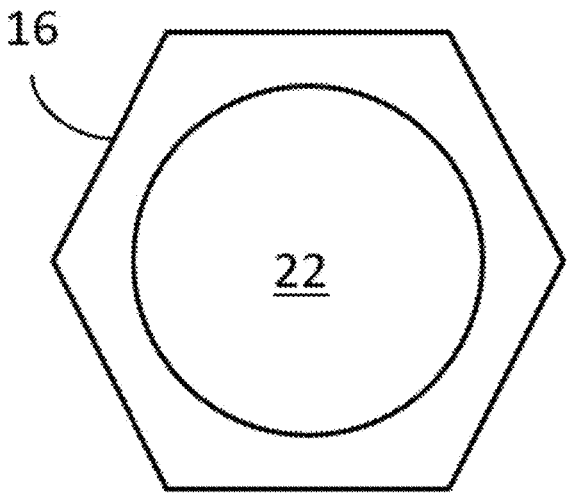
FIG. 7 illustrates an end elevation view of a graspable suction tip with a hexagonal cross section, in accordance with some embodiments of the disclosure.
Figure 8:
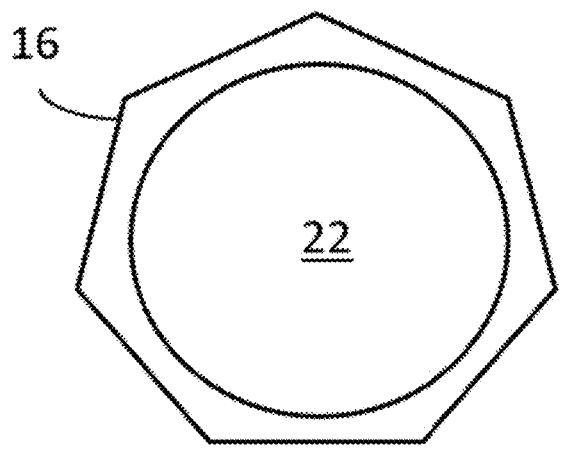
FIG. 8 illustrates an end elevation view of a graspable suction tip with a heptagonal cross section, in accordance with some embodiments of the disclosure.
Figure 9:
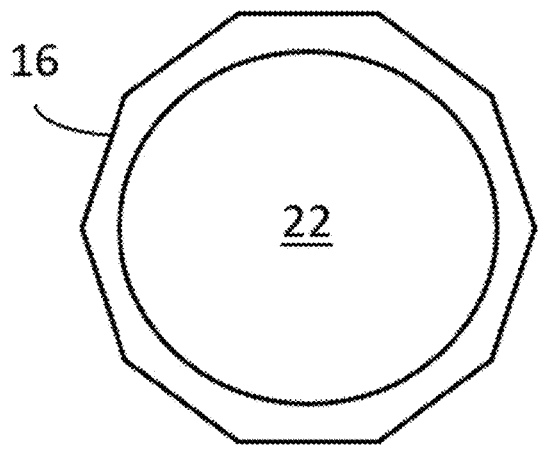
FIG. 9 illustrates an end elevation view of a graspable suction tip with a decagonal cross section, in accordance with some embodiments of the disclosure.
Figure 10:
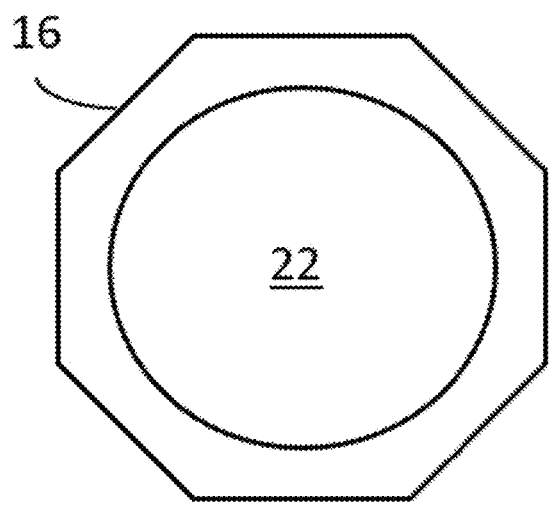
FIG. 10 illustrates an end elevation view of a graspable suction tip with an octagonal cross section, in accordance with some embodiments of the disclosure.
Figure 11:
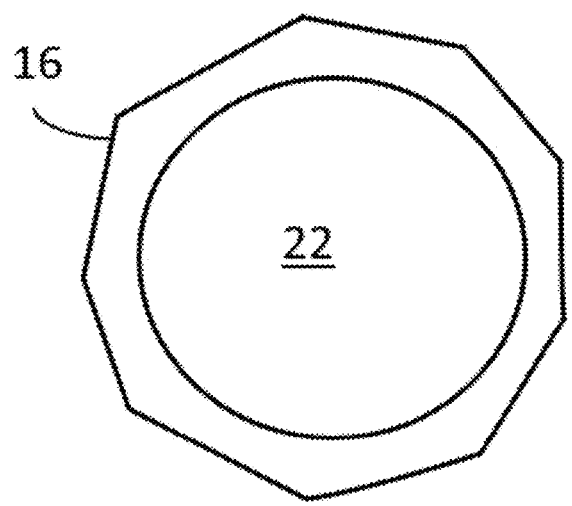
FIG. 11 illustrates an end elevation view of a graspable suction tip with a nonagonal cross section, in accordance with some embodiments of the disclosure.

Turning now to the drawings to illustrate example embodiments of the present disclosure, FIGS. 1 and 2 show grasper receiving section 12 which comprises distal portion 16 having a proximal end 18 and coupled to a male device adaptor 20. Distal portion 16 comprises a set of diversion holes 46, configured to provide an alternative fluid pathway for liquid or air. Male device adaptor 20 is inserted into a lumen in the device 14 (tubing 70, as shown in FIG. 18B, for example), as shown for example in FIG. 4. Lumen 22 extends through grasper receiving section 12 and device 14, as shown, for example, in FIGS. 4-5. Grasper receiving section 12 and tubing 70, shown for example in FIGS. 17A and 17D, are configured to be grasped by a surgical instrument such as a pair of graspers.

In some embodiments, male device adaptor 20 is greater in length than distal portion 16 of grasper receiving section 12 and is configured to extend an operatively selected distance into lumen 22 of device 14. Operatively selected distance is the distance sufficient enough to provide secure bonding between proximal portion 18 (male device adaptor 20) and tubing 70, for example. An internal stop may be provided to limit the distance that male device adaptor 20 extends into lumen 22 of device 14. Male device adaptor 20 may be bonded at the desired distance within device 14, for example, to maximize graspability. In some embodiments, adaptor 20 may be of equal or shorter length than distal portion 16. In some embodiments, male device adaptor 20 is configured to have an external diameter slightly larger than the internal diameter of lumen 22 of device 14, providing a secure friction fit. In some embodiments, adaptor 20 may be secured with an interference or fricative friction fit. In some embodiments, adaptor 20 may be secured by adhesive, bonded, ultrasonically bonded, thermoformed, or otherwise secured. In some embodiments, the external diameter of adaptor 20 need not be larger than that of the internal diameter of the lumen 22 of the tubular surgical device 14 (tubing 70) if adhesive or other attachment is provided securing adaptor 20 within the lumen 15 of device 14. In some embodiments, lumen 15 may be configured with a latching system configured to mate to male device adaptor 20. Following insertion of male device adaptor 20 into device 14, a set of protrusions conform to a snap fit, locking in male device adaptor 20 to device 14.

In one embodiment, the grasper receiving section 12 is configured of a unitary piece of material, while in other embodiments more materials may be employed. In one embodiment where multiple materials are employed, the male device adaptor 20 may be manufactured from a material having a higher durometer than that of the distal portion 16. Such a higher durometer material may be a plastic, thermoset resin, composite material or a metal tube. Suitable metals include but are not limited to steel or stainless steel.

Figure 3:
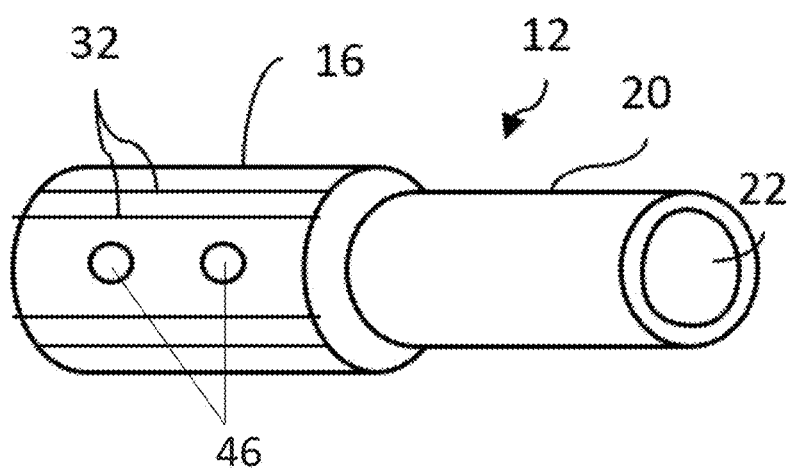
FIG. 3 illustrates a perspective view of a graspable suction tip wherein its distal portion has a textured exterior, in accordance with some embodiments of the disclosure.
Figure 17A:
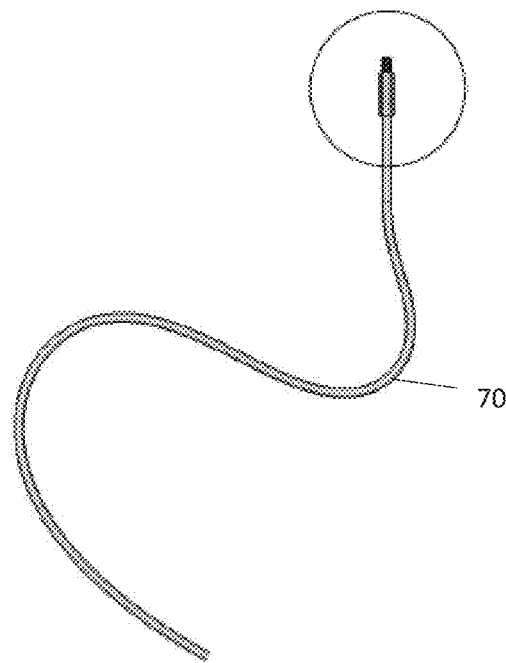
FIG. 17A illustrates a side view of a graspable suction tip comprising a cylindrical section positioned outside the tubing and distal portion, in accordance with some embodiments of the disclosure.
Figure 17B:
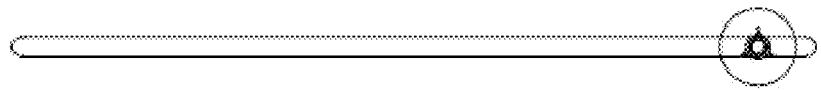
FIGS. 17B-C illustrate a front view of a graspable suction tip comprising a cylindrical section positioned outside the tubing and distal portion, in accordance with some embodiments of the disclosure.
Figure 17C:
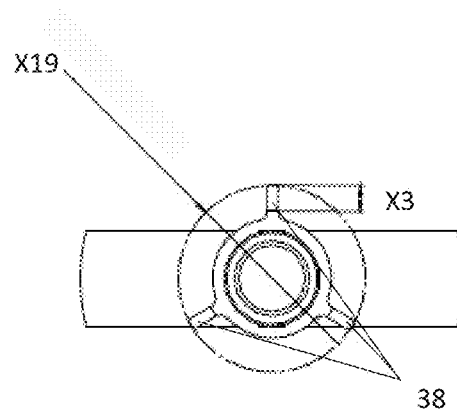
Figure 17D:
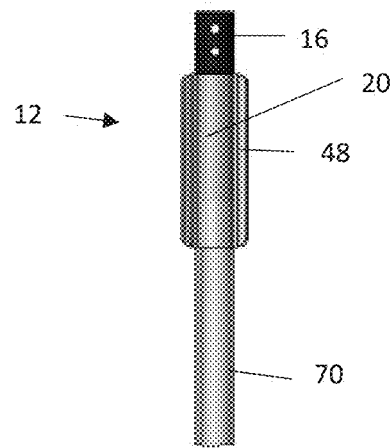
FIG. 17D illustrates a side view of a distal region of a graspable suction tip with a graspable suction tip comprising a cylindrical section positioned outside the tubing and distal portion, in accordance with some embodiments of the disclosure.

In one embodiment, the device 14 is a suction or irrigation tube, such as tubing 70, shown for example in FIGS. 17A and 17D. In such an embodiment, the male device adaptor 20, disposed within lumen 15 of tubing 70 provides additional structural support allowing the grasper to grasp and hold the device 14. In one embodiment, such as that illustrated in FIG. 4, the exterior of device 14 is smooth. In an alternative embodiment, such as that illustrated in FIG. 5, device 14 may be configured with a series of flutes 30 disposed around its outside circumference and along its major axis. Flutes 30 are grooves running along the longitudinal axis of at the exterior surface to provide friction when grasped by a surgical instrument. For example, the coefficient of kinetic friction, $\mu_k$, provided by flutes 30 may be in the range of 0.04 to 0.8, 0.2 to 0.6, 0.3 to 0.5, 0.35 to 0.4, or 0.04 to 0.6. Flutes 30 are configured to provide surface roughness. Alternatively, as in FIG. 3, flutes 32 may be disposed in a pattern or spaced configuration around the exterior of the distal portion 16. Other textures may also be suitable, either for application to distal portion 16, proximal portion 18, wings, or to device 14. For example, a set of diagonally opposed lines, a dimpled surface, and/or knurling may be provided to encourage friction during grasping. In some embodiments, an elevated edge or lip may be provided at one or more edges of a swept wing, flexible wing, or wing to encourage friction during grasping.

Figure 13:
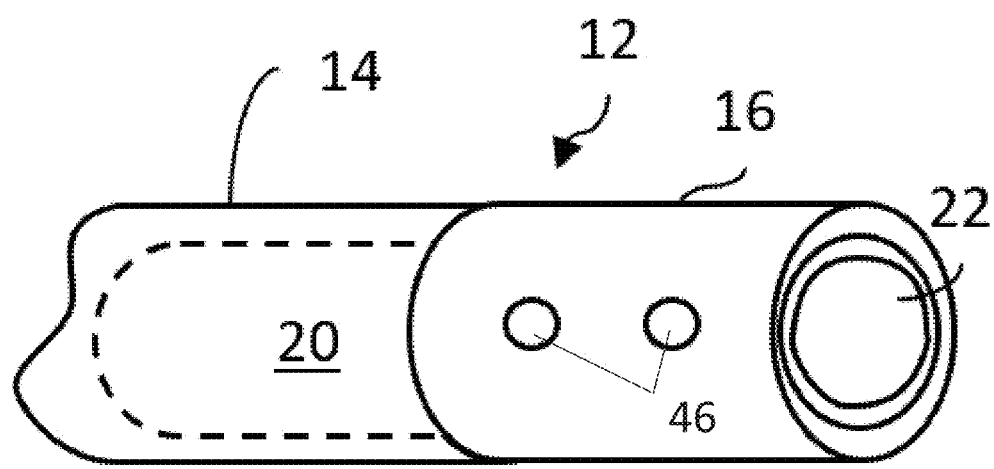
FIG. 13 illustrates a perspective view of a graspable suction tip with circumferential layers provided at a distal portion, in accordance with some embodiments of the disclosure.

In one such embodiment the male device adaptor 20 has a higher durometer than device 14. In various embodiments, the durometer of grasper receiving section 12 has a Shore durometer of between 30D and 70D, between 70D and 95D, between 95D and 150D, or between 30D and 150D, allowing for gripping of distal portion 16 without causing either crushing or slippage. In some embodiments, wings may be configured with a lower durometer than the rest of grasper receiving section 12. The material from which the grasper receiving section 12, including any wings extending therefrom, is configured is biocompatible and may be selected from the group of materials comprising polyurethanes, aliphatic or semialiphatic polyamides, polysulfone, silicone, and block copolymers made up of rigid polyamide blocks and soft polyether blocks (i.e. PEBAX®). The tubing, and any wings extending therefrom, likewise may be from a number of other materials, including polyvinyl chloride tubing, polyurethane tubing, or silicone tubing. In one embodiment, illustrated in FIG. 13, the distal portion 16 is formed by co-extrusion of a material having higher durometer on the interior with a lower durometer exterior. The illustrated embodiment of FIG. 13 shows a two-layer co-extrusion. Other embodiments may have three, four, five, or more co-extruded layers. In some embodiments, grasper receiving section 12 may comprise, additionally or alternatively, stainless steel, polycarbonate (i.e. LEXAN®), polyvinyl chloride (PVC) (either rigid or flexible forms), acrylonitrile butadiene styrene (ABS), pebax block copolymers made up of rigid polyamide blocks and soft polyether blocks (i.e. PEBAX®), and/or acrylic.

Figure 12:
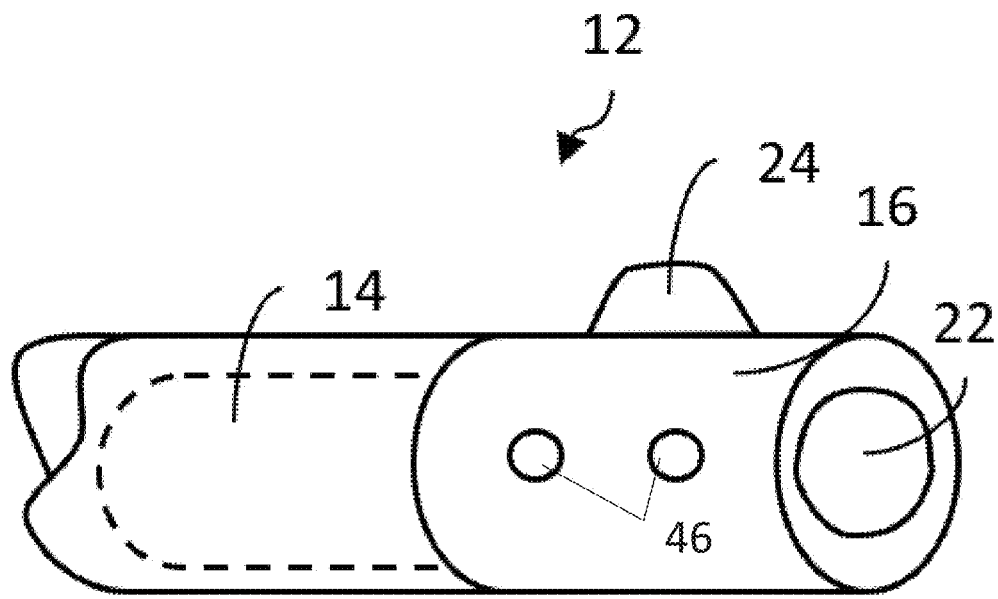
FIG. 12 illustrates a perspective view of a graspable suction tip with a wing disposed on the distal portion, in accordance with some embodiments of the disclosure.

The end piece may have a round cross section as in FIGS. 1-5. Alternatively, as illustrated in FIGS. 6-11, a pentagonal, hexagonal, heptagonal, decagonal, nonagonal, or octagonal cross section may be provided. One or more wings 24 may be disposed on distal portion 16 to facilitate grasping, as in the embodiment illustrated in FIG. 12. In the illustrated embodiment of FIG. 12, wing 24 is a singular symmetrical wing disposed in line with the longitudinal axis.

Figure 14A:
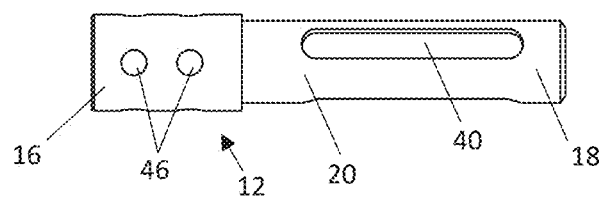
FIGS. 14A-B illustrate a side view of a graspable suction tip with longitudinal slots formed in the male device adaptor, in accordance with some embodiments of the disclosure.
Figure 14B:
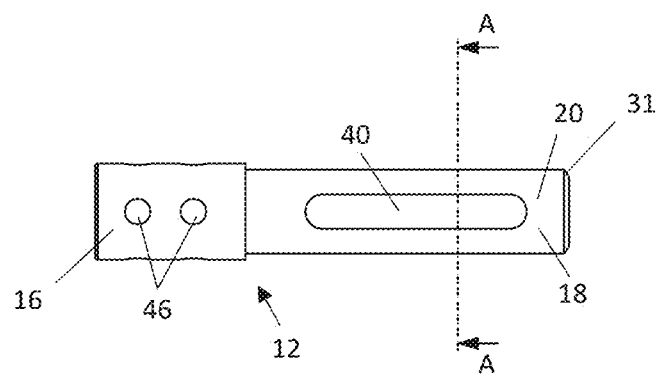
Figure 14C:
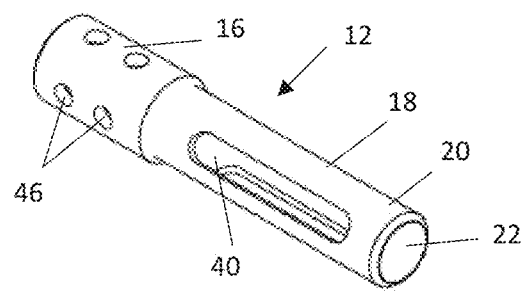
FIG. 14C illustrates a perspective view of a graspable suction tip with longitudinal slots formed in the male device adaptor, in accordance with some embodiments of the disclosure.
Figure 14D:
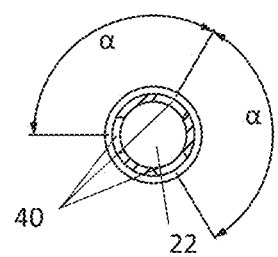
FIG. 14D illustrates a cross-sectional plan view, taken along line A-A of FIG. 14B, of a graspable suction tip with longitudinal slots formed in the male device adaptor, in accordance with some embodiments of the disclosure.
Figure 15A:
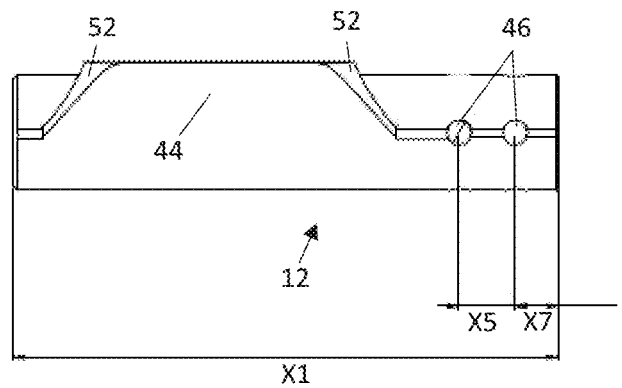
FIG. 15A illustrates a side view of a graspable suction tip comprising a flexible wing, in accordance with some embodiments of the disclosure.
Figure 15B:
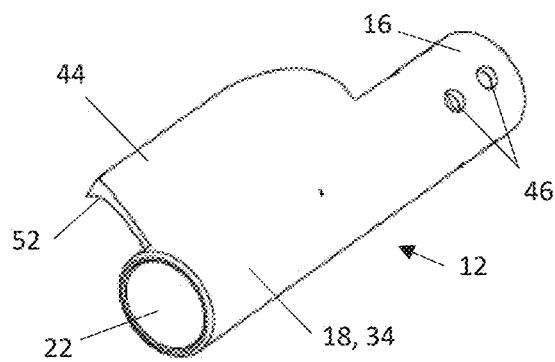
FIG. 15B illustrates a perspective view of a graspable suction tip comprising a flexible wing, in accordance with some embodiments of the disclosure.
Figure 15C:
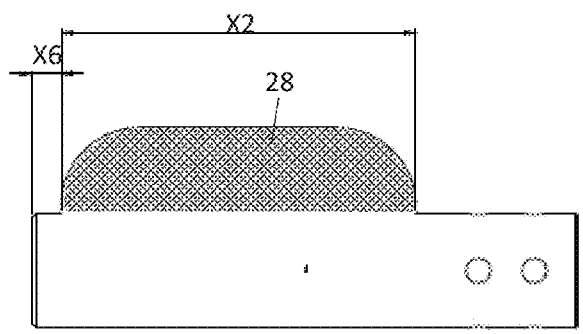
FIG. 15C illustrates a side view of a graspable suction tip comprising a flexible wing, in accordance with some embodiments of the disclosure.
Figure 15D:
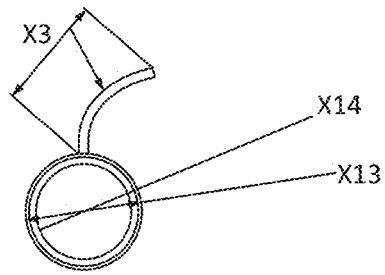
FIG. 15D illustrates a cross-sectional plan view of a graspable suction tip comprising a flexible wing, in accordance with some embodiments of the disclosure.
Figure 18A:
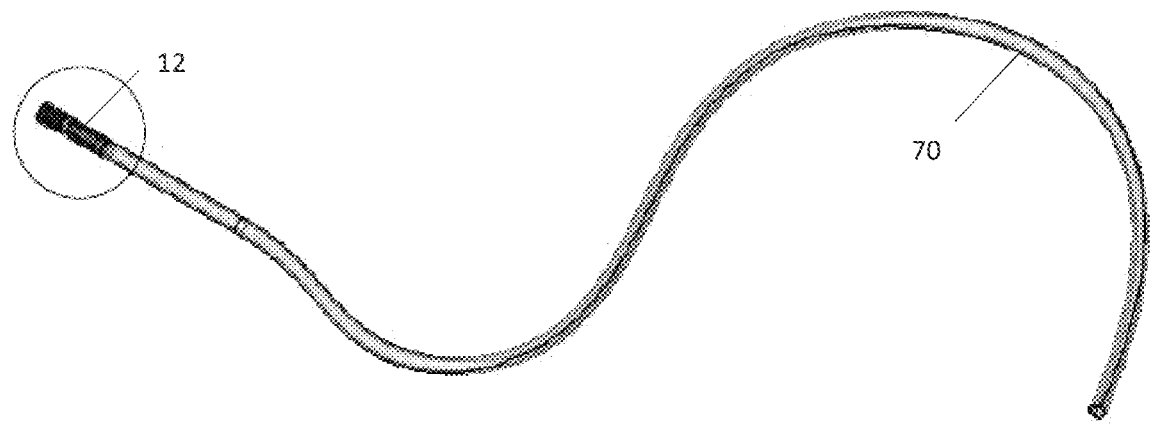
FIG. 18A illustrates a side view of a graspable suction tip with longitudinal slots formed in the male device adaptor, the male adaptor positioned inside tubing, in accordance with some embodiments of the disclosure.
Figure 18B:
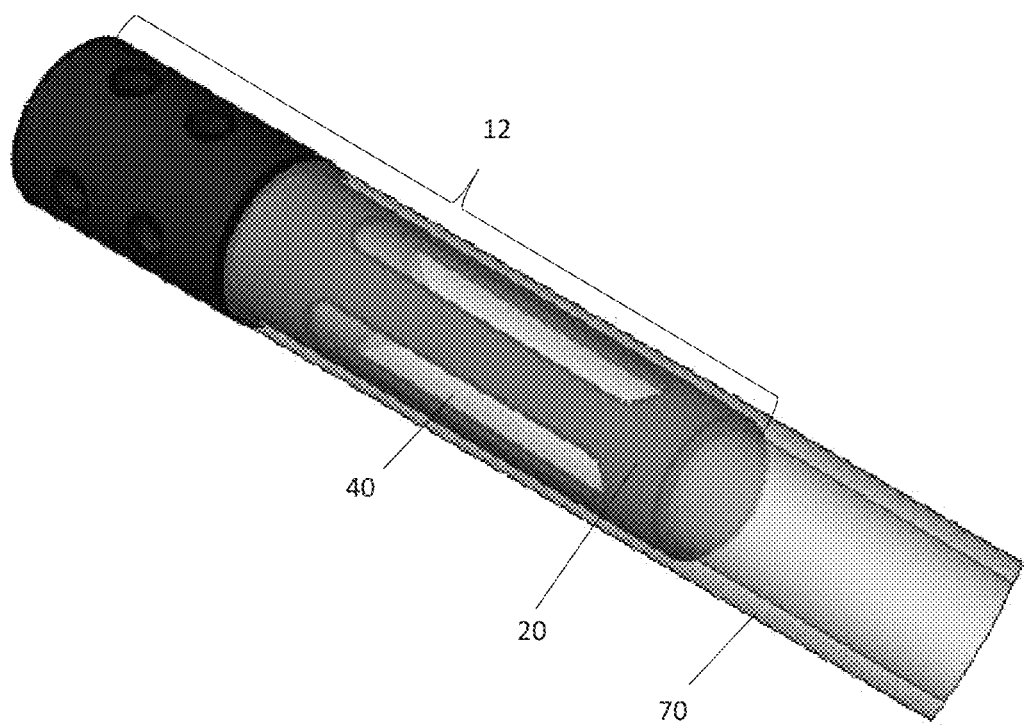
FIG. 18B illustrates a perspective view of a graspable suction tip with longitudinal slots formed in the male device adaptor, the male adaptor positioned inside tubing, in accordance with some embodiments of the disclosure.
Figure 19A:
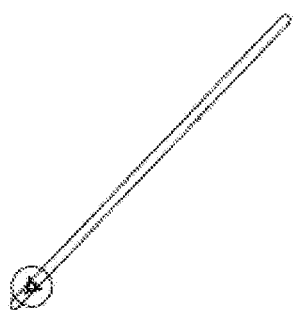
FIGS. 19A illustrates a front view of a graspable suction tip with the male adaptor positioned inside tubing, in accordance with some embodiments of the disclosure.
Figure 19B:
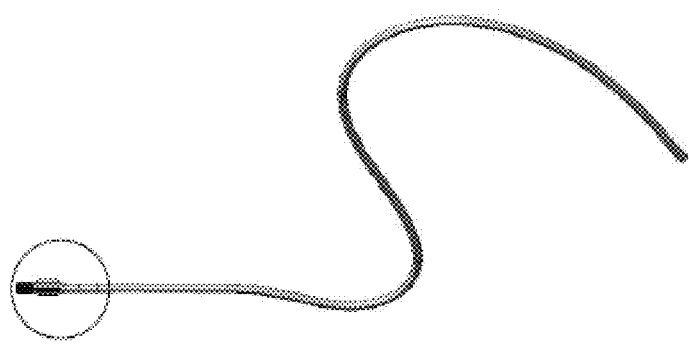
FIG. 19B is a side view of a graspable suction tip with the male adaptor positioned inside tubing, in accordance with some embodiments of the disclosure.
Figure 19C:
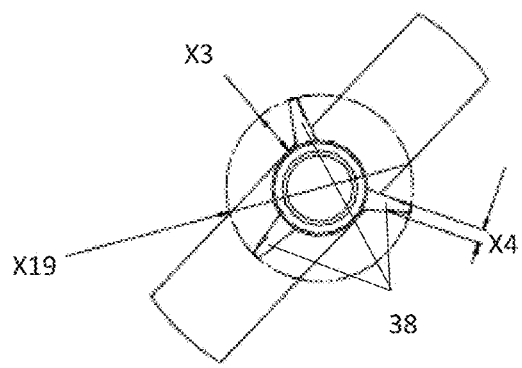
FIG. 19C illustrates a front view of a graspable suction tip with the male adaptor positioned inside tubing, in accordance with some embodiments of the disclosure.
Figure 19D:
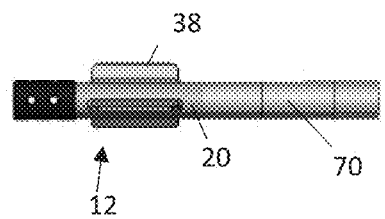
FIG. 19D illustrates a side view of a graspable suction tip with the male adaptor positioned inside tubing, in accordance with some embodiments of the disclosure.
Figure 20A:
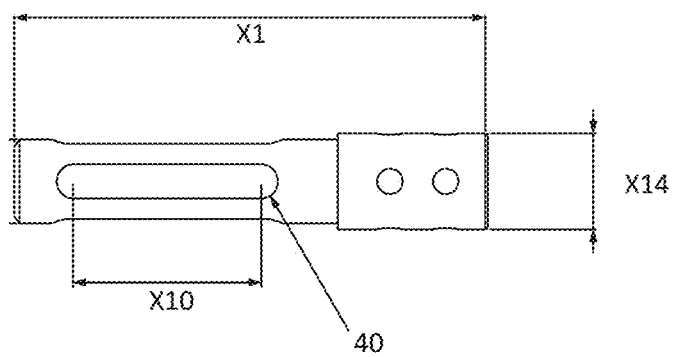
FIGS. 20A-B illustrate side views of a graspable suction tip with longitudinal slots formed in the male device adaptor, in accordance with some embodiments of the disclosure.
Figure 20B:
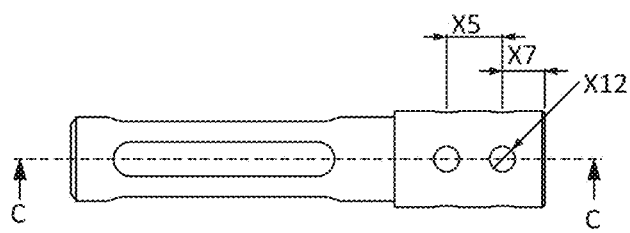
Figure 20C:
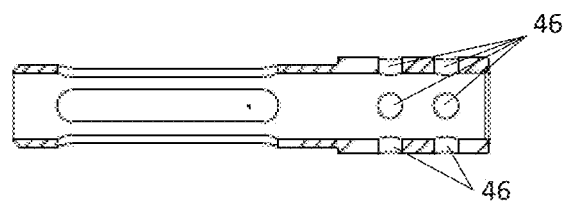
FIG. 20C illustrates a sectional view along line C-C of FIG. 20B and a cross-sectional view of a graspable suction tip with longitudinal slots formed in the male device adaptor, in accordance with some embodiments of the disclosure.
Figure 20D:
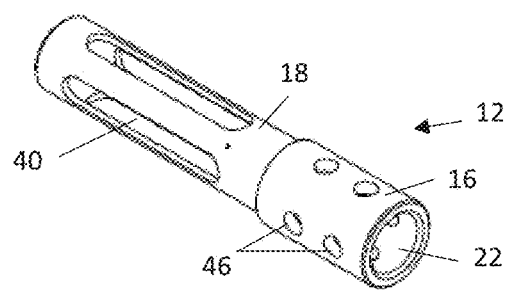
FIG. 20D illustrates a perspective view of a graspable suction tip with longitudinal slots formed in the male device adaptor, in accordance with some embodiments of the disclosure.
Figure 20E:
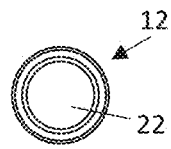
FIG. 20E illustrates a cross-sectional view of a graspable suction tip with longitudinal slots formed in the male device adaptor, in accordance with some embodiments of the disclosure.
Figure 21A:
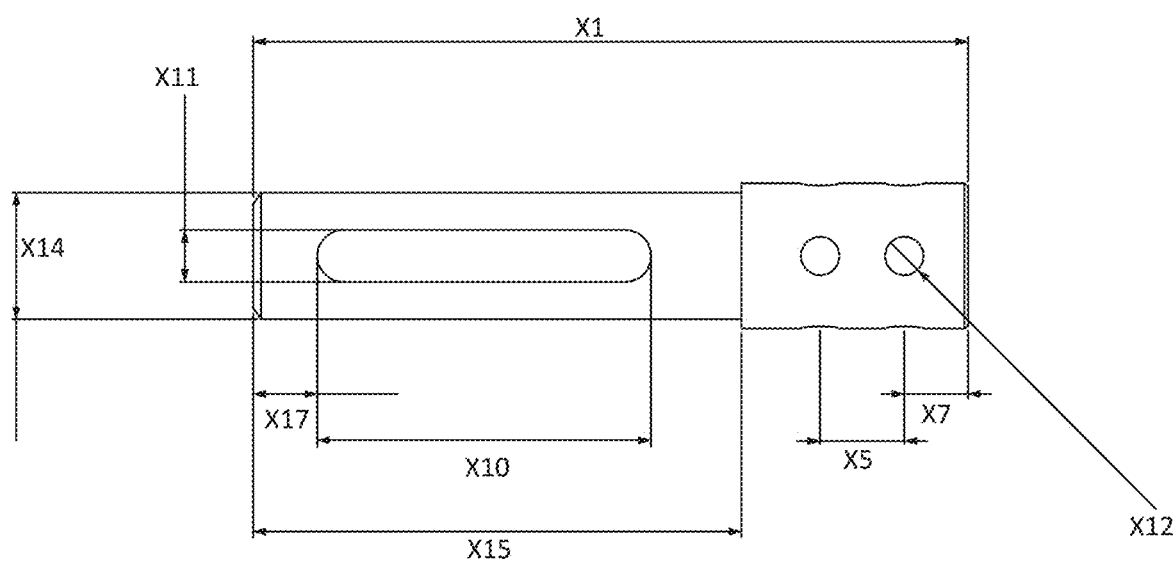
FIG. 21A illustrates a side view of a graspable suction tip with longitudinal slots formed in the male device adaptor, in accordance with some embodiments of the disclosure.
Figure 21B:
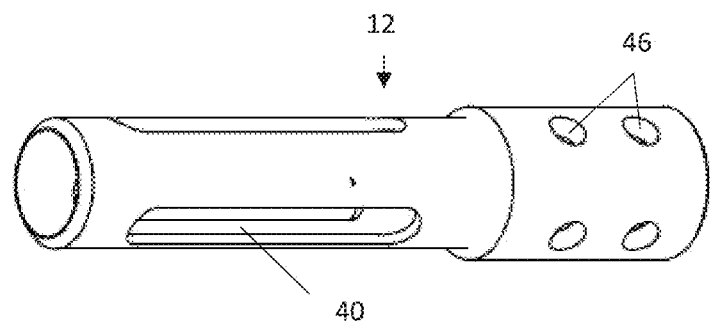
FIG. 21B illustrates a perspective view of a graspable suction tip with longitudinal slots formed in the male device adaptor, in accordance with some embodiments of the disclosure.
Figure 21C:
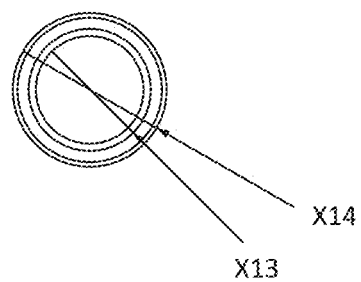
FIG. 21C illustrates a cross-sectional plan view of a graspable suction tip with longitudinal slots formed in the male device adaptor, in accordance with some embodiments of the disclosure.
Figure 22A:
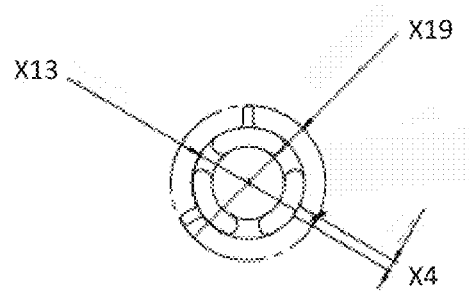
FIG. 22A illustrates a cross-sectional plan view of a graspable suction tip with longitudinal slots formed in a distal portion and wings positioned at a proximal end, in accordance with some embodiments of the disclosure.
Figure 22B:
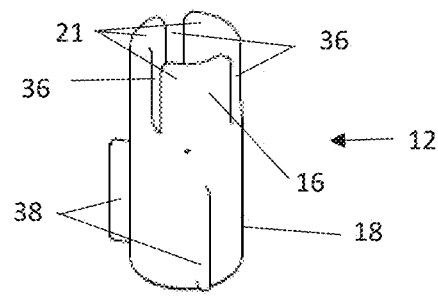
FIG. 22B illustrates a perspective view of a graspable suction tip with longitudinal slots formed in a distal portion and wings positioned at a proximal end, in accordance with some embodiments of the disclosure.
Figure 22C:
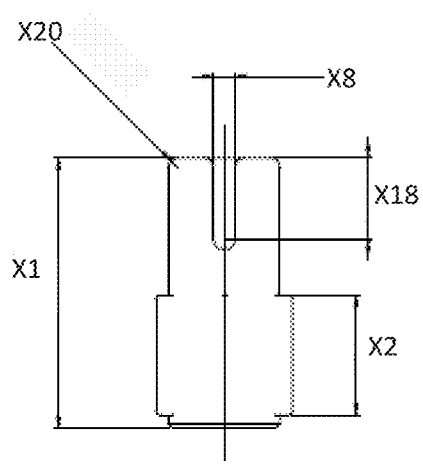
FIGS. 22C-D illustrate a side view of a graspable suction tip with longitudinal slots formed in a distal portion and wings positioned at a proximal end, in accordance with some embodiments of the disclosure.
Figure 22D:
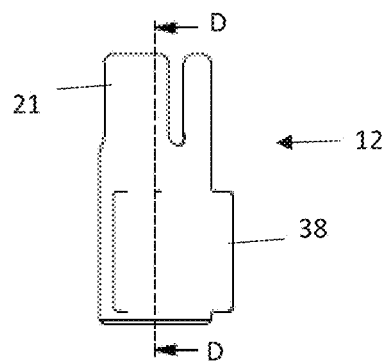
Figure 22E:
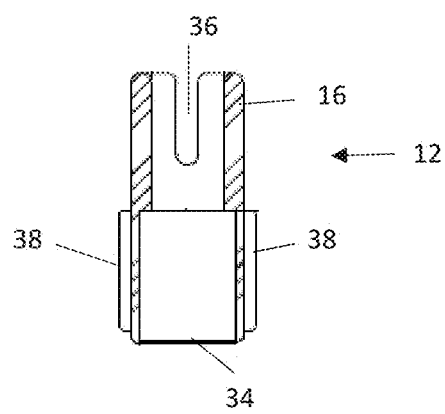
FIG. 22E illustrates a sectional view along line D-D in FIG. 22D and a longitudinal cross-sectional view of a graspable suction tip with longitudinal slots formed in a distal portion and wings positioned at a proximal end, in accordance with some embodiments of the disclosure.
Figure 23A:
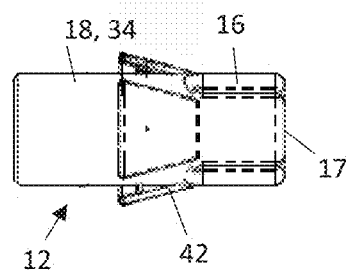
FIGS. 23A-B illustrate a side view of a graspable suction tip configured with swept wings, in accordance with some embodiments of the disclosure.
Figure 23B:
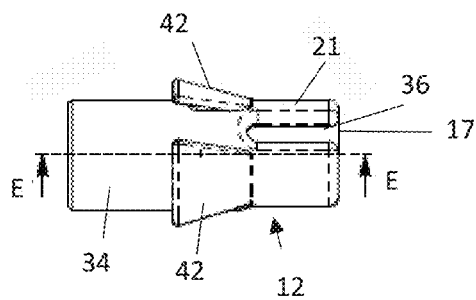
Figure 23C:
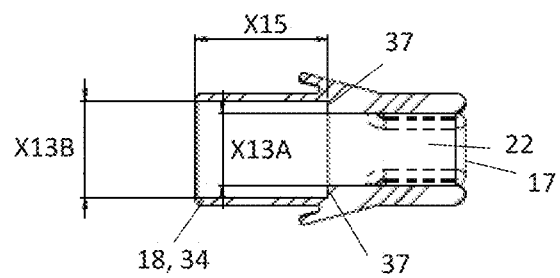
FIG. 23C illustrates a longitudinal cross-sectional view of a graspable suction tip configured with swept wings, in accordance with some embodiments of the disclosure.
Figure 23D:
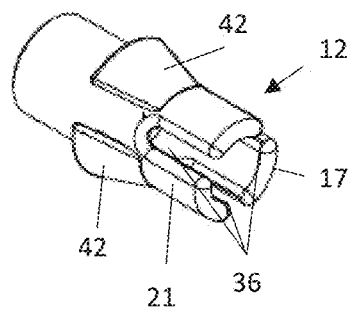
FIG. 23D illustrates a perspective view of a graspable suction tip configured with swept wings, in accordance with some embodiments of the disclosure.
Figure 23E:
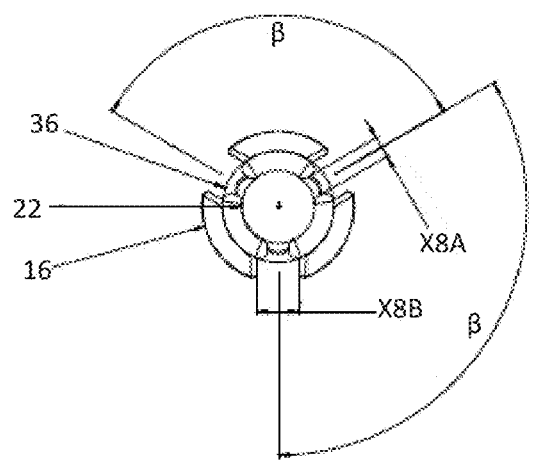
FIG. 23E illustrates a cross-sectional plan view of a graspable suction tip configured with swept wings, in accordance with some embodiments of the disclosure.
Figure 24A:
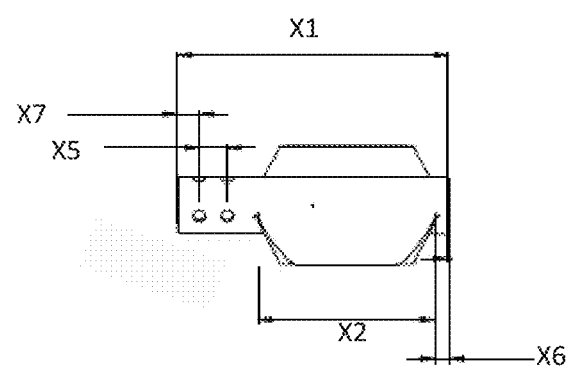
FIG. 24A illustrates a side view of a graspable suction tip comprising dual wings, in accordance with some embodiments of the disclosure.
Figure 24B:
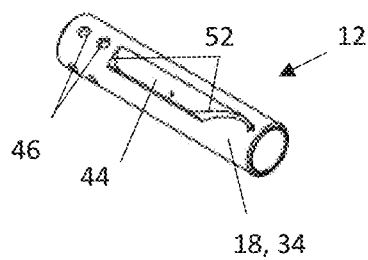
FIG. 24B illustrates a perspective view of a graspable suction tip comprising dual wings, in accordance with some embodiments of the disclosure.
Figure 24C:
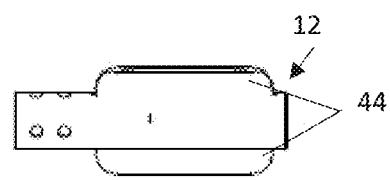
FIG. 24C illustrates a side view of a graspable suction tip comprising dual wings, in accordance with some embodiments of the disclosure.
Figure 24D:
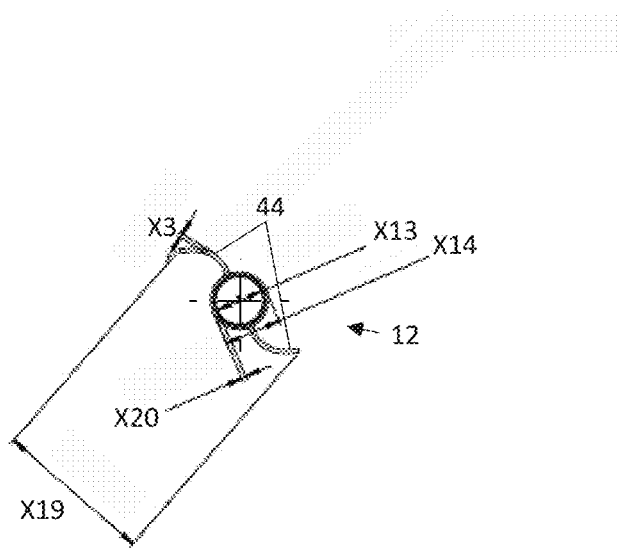
FIG. 24D illustrates a cross-sectional plan view of a graspable suction tip comprising dual three wings, in accordance with some embodiments of the disclosure.

FIGS. 14A-D and FIGS. 21A-C illustrate a grasper receiving section 12 with three longitudinal slots 40 formed in the male device adaptor 20. Diversion holes 46 are positioned within distal portion 16, to help minimize or prevent damage to tissue from suction forces applied toward a single distal opening of lumen 22. Diversion holes 46 are configured to provide alternate flow paths for suction, irrigation, and/or insufflation. FIG. 14B illustrates tapered contour 31 cut at an angle into the circumference of the proximal end of grasper receiving section 12 for ease of insertion into the tubular surgical device. FIG. 14D illustrates that each of the longitudinal slots are positioned equidistant from the other longitudinal slots, each being separated by an angle α about the circumference of proximal end 18. In the illustrated embodiments, angle α is equal to 120°. In the embodiment shown in FIGS. 14A-D, male device adaptor 20 is configured for insertion into tubing 70, as shown in FIGS. 18A-B. FIGS. 18A-B shows grasper receiving section 12 with longitudinal slots 40 formed in the male device adaptor 20 and male device adaptor 20 positioned inside tubing 70.

FIGS. 15A-D illustrate an example embodiment wherein grasper receiving section 12 comprises a single flexible wing 44 and proximal portion 18 is configured with a female device adaptor 34. Diversion holes 46 are positioned in distal portion 16. FIGS. 24A-D shows an alternative embodiment wherein grasper receiving section 12 comprises a pair of flexible wings 44 and proximal portion 18 is configured with female device adaptor 34. In each of these embodiments (FIGS. 15A-D and 24A-D), flexible wing 44 is provided with an arcuate contour 52 on an edge of both a proximal and distal end, as shown in FIGS. 15A-B and 24A-B. Arcuate contour 52 is configured to provide a low-profile during insertion into and extraction from a robotic surgery or laparoscopic surgery port, into another surgical device, or directly into patient anatomy. In some embodiments, flexible wing 44 may be provided with a single arcuate contour 52. In some embodiments, as illustrated for example in FIG. 15C, wings may be provided with a textured surface comprising knurling 28.

Figure 16A:
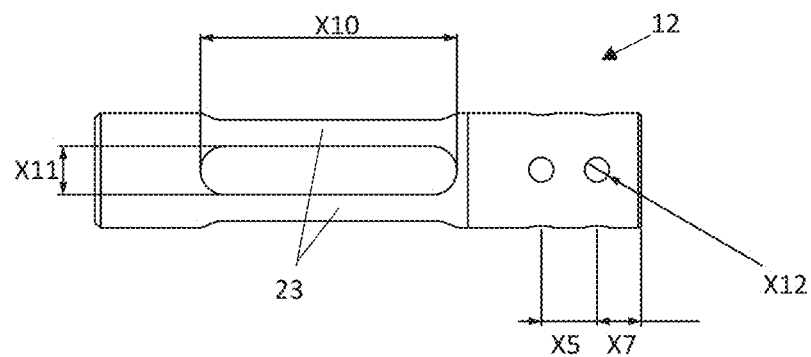
FIGS. 16A-B illustrate a side view of a graspable suction tip with longitudinal slots formed in the male device adaptor, in accordance with some embodiments of the disclosure.
Figure 16B:
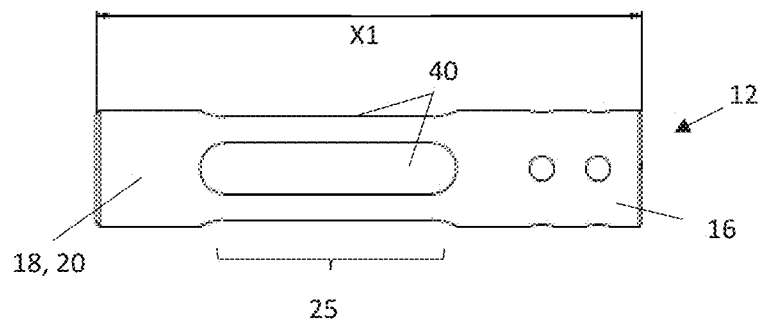

FIGS. 16A-D shows an alternative embodiment of a grasper receiving section 12 with four longitudinal slots 40 formed in female device adaptor 34, wherein proximal end 18 is configured to surround tubing 70. FIGS. 16A-B illustrate an embodiment wherein a side profile view reveals a wider distal portion 16, wider proximal portion 18, and narrower central portion 25 surrounding longitudinal slots 40. In the illustrated embodiment of FIGS. 16A-B, the circumference of the central portion 25 including longitudinal slots is smaller than the circumference of the distal portion 16 and proximal portion 18 of grasper receiving section 12, forming a dumbbell shape. In this embodiment, proximal portion 18 is a male device adaptor 20, configured with an external diameter less than or equal to the internal diameter of tubing 70, the tubular surgical device. During use, a user may grasp at the longitudinal slots that are covered by the surgical tubing.

Figure 16C:
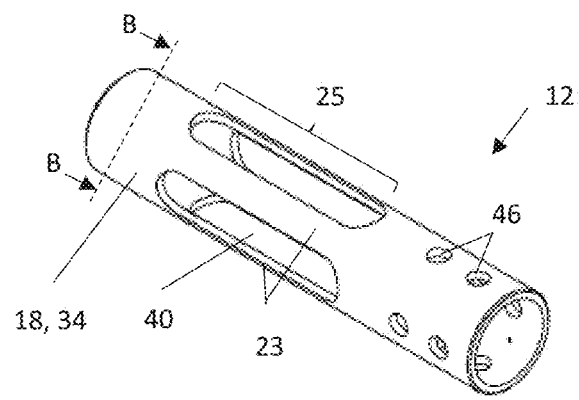
FIG. 16C illustrates a perspective view of a graspable suction tip with longitudinal slots formed in the female device adaptor, in accordance with some embodiments of the disclosure.
Figure 16D:
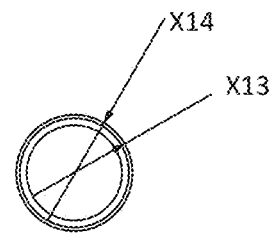
FIG. 16D illustrates a cross-sectional plan view taken along line B-B of FIG. 16C of a graspable suction tip with longitudinal slots formed in the female device adaptor, in accordance with some embodiments of the disclosure.

FIGS. 16C-D illustrate an embodiment wherein a perspective view reveals a constant outer circumference, with longitudinal slots 40 and diversion holes 46 cut through the outer wall. In the illustrated embodiments of FIGS. 16C-D, proximal portion 18 is a female device adaptor 34 which is configured with an external diameter that is greater than or equal to the internal diameter of tubing 70, the tubular surgical device. In some embodiments, tubing 70 may only be inserted into proximal portion 18. In this configuration, surgical instruments may be inserted into longitudinal slots 40 to grasp onto one or more vanes 23.

FIGS. 17A-D shows grasper receiving section 12 comprising cylindrical section 48 positioned outside tubing 70 and distal portion 16. Cylindrical section 48 may be molded separately or may be molded together with tubing 70. In the case where cylindrical section 48 is molded separately, adhesive or bonding may be used to secure cylindrical section 48 in place around tubing 70. Male device adaptor 20 may be configured to seat inside tubing 70 while cylindrical section 48 seats on the outside of tubing 70. In the embodiment illustrated in FIGS. 17A-D, cylindrical section 48 is configured with three wings 38 extending along the longitudinal axis and positioned equidistant circumferentially. In alternative embodiments, wings may be positioned in a non-equidistant wing arrangement about the circumference of grasper receiving section 12. A further alternative to this design allows for the wings 38 to be molded or extruded directly as part of tubing 70.

FIGS. 19A-D show grasper receiving section 12 with male device adaptor 20 positioned inside tubing 70. In the embodiment illustrated in FIGS. 19A-D, tubing 70 is configured with a set of three wings 38 positioned equidistant circumferentially in a region adjacent to male device adaptor 20. Various alternatives of male device adaptor 20, as disclosed herein, are contemplated.

FIGS. 18A-B and 20A-E show an alternative embodiment wherein grasper receiving section 12 is provided with four longitudinal slots 40 formed in male device adaptor 20, wherein proximal end 18 is configured to be inserted into tubing 70.

The embodiment shown in FIGS. 22A-E includes grasper receiving section 12 with grooves 36 formed in distal portion 16 and wings 38 positioned at proximal portion 18. In the illustrated embodiment, proximal portion 18 is configured as a female device adaptor 34. Grooves 36 extend along the longitudinal axis of the device and intersect with the distal most end 17 and terminate some distance away from wings 38. In the illustrated embodiment of FIGS. 22A-E, a set of three wings 38 extend from proximal portion 18 and a set of three grooves 36 in distal portion 16 form a set of three distally extending fingers 21. Fingers 21 are configured to provide a similar advantage as diversion holes 46 in providing an alternative fluid pathway during suction, irrigation, and/or insufflation.

The embodiment shown in FIGS. 23A-E includes grasper receiving section 12 configured with swept wings 42. Swept wings 42 are configured to provide a low-profile during insertion into a robotic surgery or laparoscopic surgery port, into another surgical device, or directly into patient anatomy. In the illustrated embodiment of FIGS. 23-A-E, distal portion 16 includes a set of three grooves 36, spaced equally from each other at angle β=120°, forming a set of three distally extending fingers 21. Grooves 36 extend along the longitudinal axis of the device and intersect with the distal most end 17 and terminate at approximately the same region as the lower profile portion of swept wings 42. In the illustrated embodiment, lumen 22 interior to grasper receiving section 12 has a stepdown 37, where the lumen is wider proximally and narrower distally.

Figure 25A:
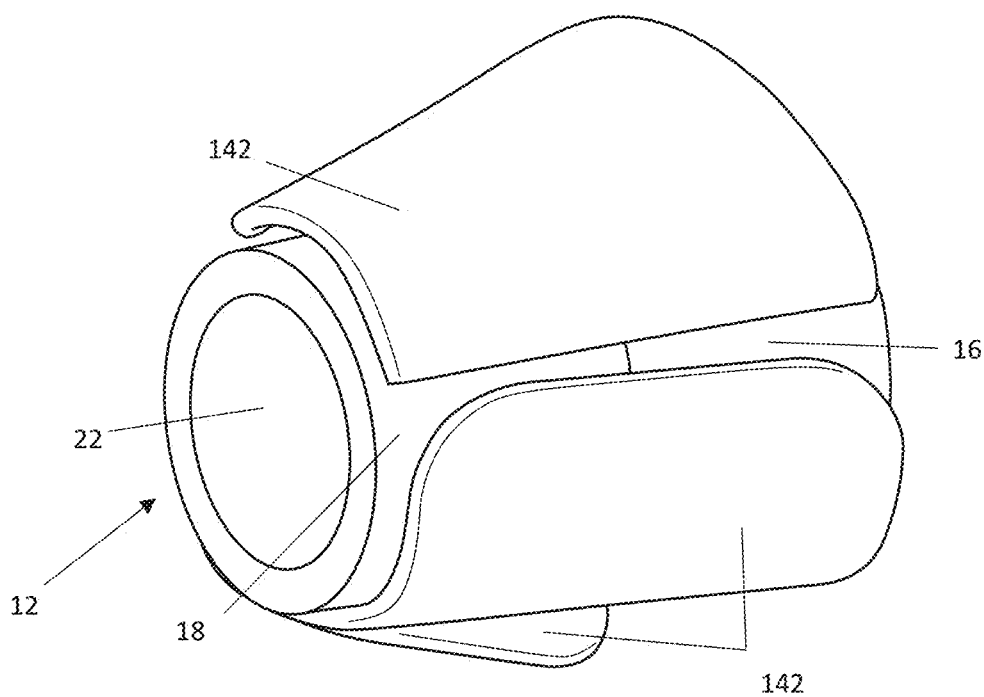
FIG. 25A illustrates a front perspective view of a graspable suction tip comprising a flexible overmold including three wings, in accordance with some embodiments of the disclosure.
Figure 25B:
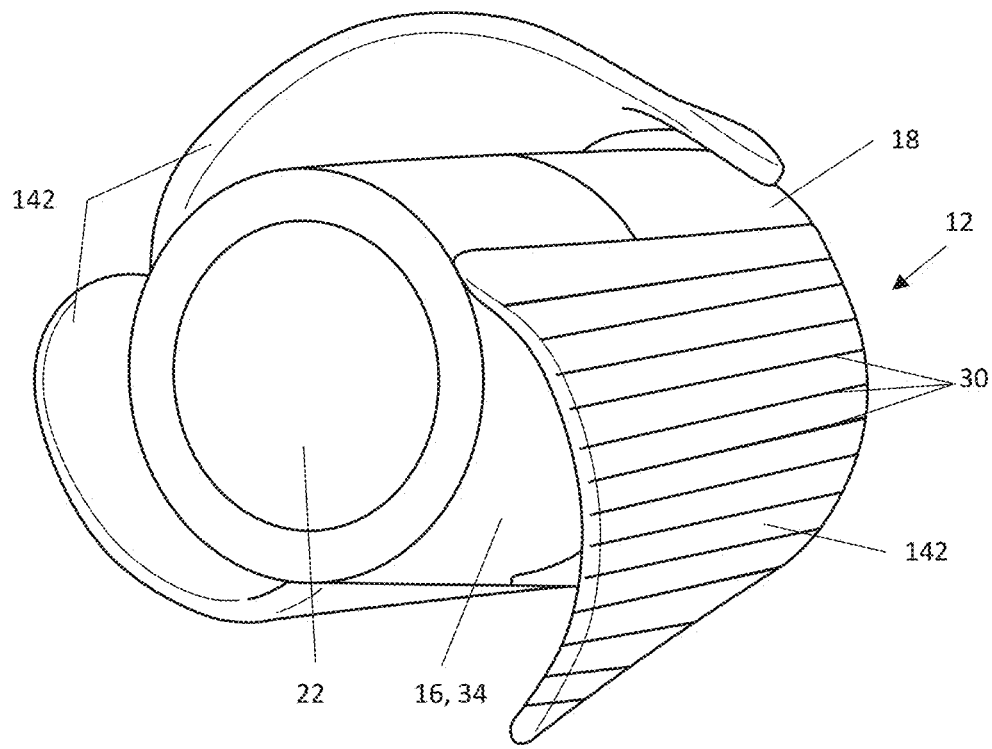
FIG. 25B illustrates a rear perspective view of a graspable suction tip comprising a flexible overmold including three wings, in accordance with some embodiments of the disclosure.

The embodiment shown in FIGS. 25A-B illustrates an overmolded section which includes a set of three swept wings 142, which extend along the length of grasper receiving section 12, from distal portion 16 to proximal portion 18. Swept wings 142 are provided with a larger outer diameter distally and a smaller outer diameter proximally, for ease of removal from a robotic surgery or laparoscopic surgery port, from another surgical device, or directly from patient anatomy. In alternate embodiments, swept wings 142 may be configured with a larger outer diameter proximally and smaller outer diameter distally. The illustrated embodiment in FIGS. 25A-B is designed to be positioned over tubing and to provide an improved graspable surface. In some embodiments, such as is shown in FIG. 25B, swept wings 142 may be provided with a textured surface configured to increase friction during grasping. FIG. 25B illustrates flutes 30 on an outer surface of swept wing 142.

Figure 26:
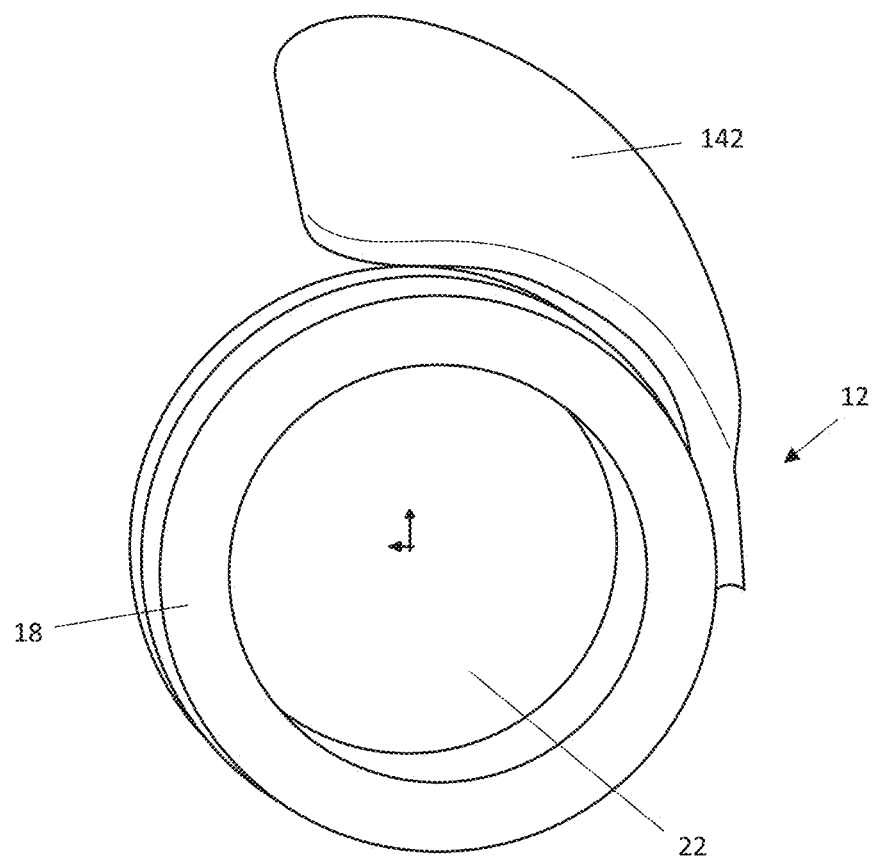
FIG. 26 illustrates a front view of a graspable, flexible overmold for the suction tip comprising one flexible wing, in accordance with some embodiments of the disclosure.

The embodiment shown in FIG. 26 illustrates an overmolded section which includes a single swept wing 142, which extends along the length from distal portion 16 to proximal portion 18. Swept wing 142 is provided with a smaller outer diameter proximally and a larger outer diameter distally, for ease of removal from a robotic surgery or laparoscopic surgery port, from another surgical device, or directly from patient anatomy. The illustrated embodiment in FIG. 26 is designed to be positioned over tubing and to provide an improved graspable surface.

Figure 27:
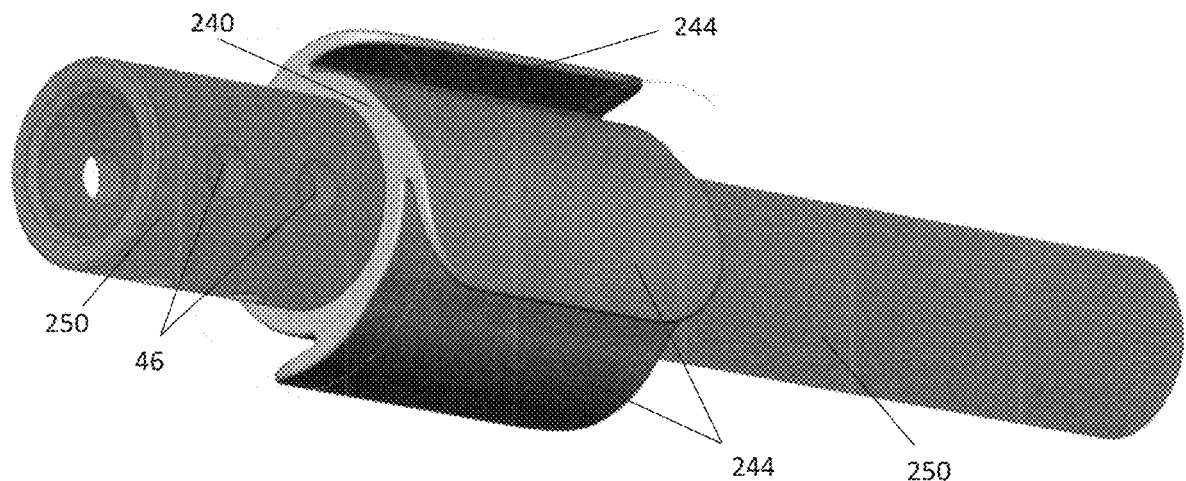
FIG. 27 illustrates a front perspective view of a graspable, flexible overmold for the suction tip comprising four flexible wings configured to extend over tubing, in accordance with some embodiments of the disclosure.

The embodiment shown in FIG. 27 illustrates a grasper receiving section comprising an overmolded section which includes tube 240 configured with a set of four wings 244. In some embodiments, wings 244 are flexible. In some embodiments, one, two, three, five, or more wings may be provided on tube 240. Tube 240 may be a molded tube configured to be slid over and friction fit to tubular portion 250. Tube 240 may be slid over, bonded, friction fit, or overmolded to tubular portion 250, the tubular surgical device. In the illustrated embodiment of FIG. 27, tubular portion 250 represents surgical tubing and is configured with a set of diversion holes 46. Diversion holes 46 are positioned on the tubular portion 250, to help minimize or prevent damage to tissue from suction forces applied toward a single distal opening of lumen 22. Diversion holes 46 are configured to provide alternate flow paths for suction, irrigation, and/or insufflation.

Figure 28:
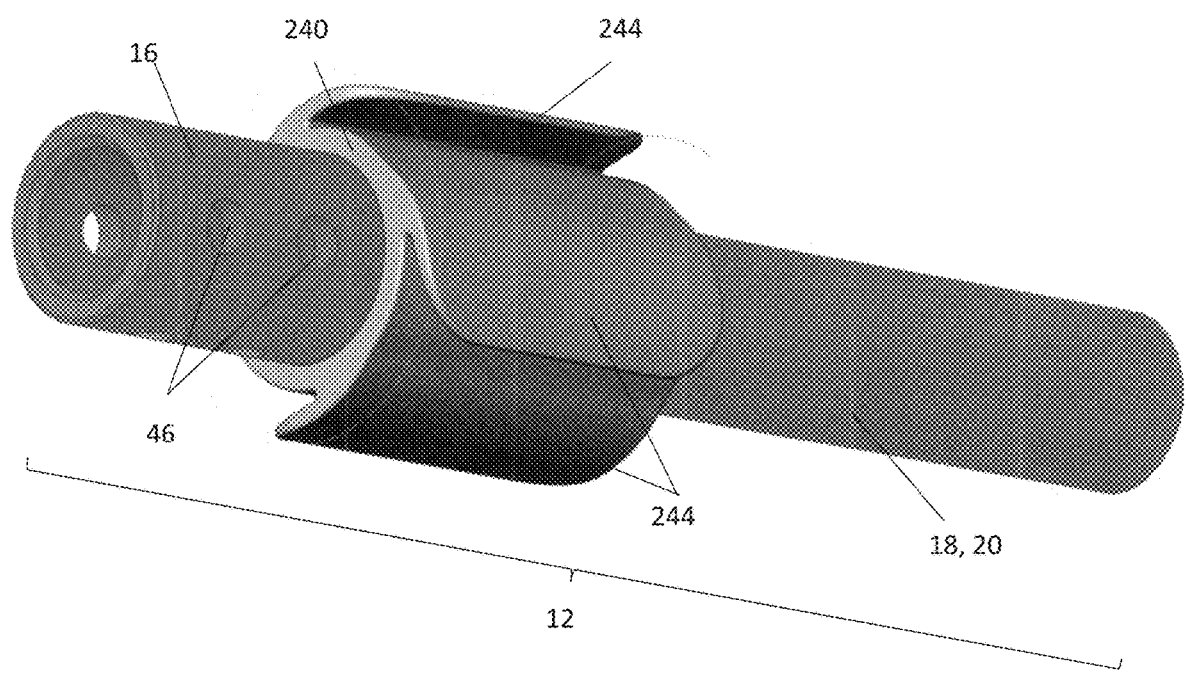
FIG. 28 illustrates a front perspective view of a graspable, flexible overmold for the suction tip comprising four flexible wings, a distal portion, and a male device adaptor positioned proximally, in accordance with some embodiments of the disclosure.

The embodiment shown in FIG. 28 illustrates a grasper receiving section comprising an overmolded section which includes tube 240 configured with a set of four wings 244. In some embodiments, wings 244 are flexible. In some embodiments, one, two, three, five, or more wings may be provided on tube 240. In the illustrated embodiment of FIG. 28, diversion holes 46 are positioned on distal portion 16 of grasper receiving section 12. to help minimize or prevent damage to tissue from suction forces applied toward a single distal opening of lumen 22. Diversion holes 46 are configured to provide alternate flow paths for suction, irrigation, and/or insufflation. In the illustrated embodiment in FIG. 28, proximal portion 18 is configured as male device adaptor 20 and is configured for receiving surgical tubing. In FIG. 28, tube 240 may be a molded tube configured to be slid over, friction fit, overmolded, and/or bonded to grasper receiving section 12.

Table 1, below, lists example lengths and angles for reference numerals listed throughout the drawings. These example lengths and angles are illustrative and various alternatives are contemplated.

TABLE 1

| Reference | Description | First Range | Second Range |
| --- | --- | --- | --- |
| α | Angle between longitudinal slots | 60-180° | 36-180° |
| β | Angle between grooves | 60-180° | 36-180° |
| X1 | Length of grasper receiving section | 0.5-1.5 inches | 0.5-2.5 inches |
| X2 | Longitudinal length of wing | 0.1-1.3 inches | 0.1-1.8 inches |
| X3 | Height of wing | 0.01-0.03 inches | 0.005-0.1 inches |
| X4 | Thickness of wing | 0.025-0.05 inches | 0.01-0.1 inches |
| X5 | Distance between the centers of diversion holes | 0.1-0.2 inches | 0.05-0.5 inches |
| X6 | Distance from wing to proximal tip | 0.05-0.075 inches | 0.01-0.1 inches |
| X7 | Distance from center of front diversion hole to distal portion | 0.01-0.3 inches | 0.001-0.75 inches |
| X8 | Width of groove | 0.01-0.1 inches | 0.001-0.5 inches |
| X8A | Inner width of groove | 0.01-0.1 inches | 0.001-0.5 inches |
| X8B | Outer width of groove | 0.05-0.2 inches | 0.01-0.5 inches |
| X10 | Length of longitudinal slot | 0.4-0.6 inches | 0.2-1.5 inches |
| X11 | Width of longitudinal slot | 0.05-0.2 inches | 0.01-0.5 inches |

TABLE 1-continued

| Reference | Description | First Range | Second Range |
|---|---|---|---|
| X12 | Diameter of diversion hole | 0.04-0.08 inches | 0.01-0.15 inches |
| X13 | Inner diameter of cross section of grasper receiving section | 0.1-0.3 inches | 0.05-0.75 inches |
| X13A | First inner diameter (includes step down from first to second inner diameter) | 0.1-0.3 inches | 0.05-0.75 inches |
| X13B | Second inner diameter | 0.1-0.4 inches | 0.05-0.75 inches |
| X14 | Outer diameter of cross section of grasper receiving section | 0.1-0.3 inches | 0.05-0.75 inches |
| X15 | Length of proximal portion of grasper receiving section | 0.3-0.8 inches | 0.1-1 inch |
| X16 | Length of distal portion of grasper receiving section | 0.1-0.4 inches | 0.05-1.5 inches |
| X17 | Distance from longitudinal slot to proximal end | 0.05-0.2 inches | 0.01-0.5 inches |
| X18 | Length of groove | 0.1-0.2 inches | 0.01-0.5 inches |
| X19 | Outer diameter of grasper receiving section including span of wings | 0.3-0.8 inches | 0.1-1.25 inches |
| X20 | Thickness of outer wall of grasper receiving section | 0.02-0.03 inches | 0.01-0.1 inches |

The foregoing description has been presented for the purposes of illustration and description. It is not intended to be exhaustive or to limit the invention to the precise form disclosed. Dimensions provided are example dimensions, various alternatives are contemplated. Many modifications and variations are possible in light of this disclosure. It is intended that the scope of the invention be limited not by this detailed description, but rather by the claims appended hereto.

What is claimed is:

1. A system for adapting a tubular surgical device for grasping by a surgical instrument, the system comprising:
a graspable component comprising:
a grasper receiving section comprised of a biocompatible material selected from polyurethanes, aliphatic or semialiphatic polyamides, polysulfone, silicone, polycarbonate, polyvinyl chloride, acrylonitrile butadiene styrene (ABS), acrylic, and block copolymers made up of rigid polyamide blocks and soft polyether blocks (PEBAX®),
the grasper receiving section formed from a unitary piece of material, the grasper receiving section comprising
a distal portion comprising one or more diversion holes
to provide an alternative fluid pathway during suction: and
a proximal portion including a male adaptor having a smaller outer diameter than the distal portion, wherein the male adaptor is configured to be disposed within a lumen of a tubular surgical device comprised of polyvinyl chloride, polyurethane, or silicone and wherein a cross section of the distal portion is formed in a shape comprising a pentagon, a hexagon, a heptagon, a nonagon, or a decagon.

2. The system of claim 1, wherein the one or more diversion holes are longitudinally aligned.

3. The system of claim 1, wherein the grasper receiving section is formed from acrylonitrile butadiene styrene (ABS).

4. The system of claim 1, wherein the grasper receiving section has a smooth exterior surface.

5. The system of claim 1, wherein the at least one pair of grooves extend along a longitudinal axis of the graspable component.

6. The system of claim 1, wherein the one or more diversion holes intersect with a distalmost end of the graspable component.

7. The system of claim 1, wherein the durometer of the graspable component is a Shore durometer of between 70D and 95D.

8. The system of claim 1, further comprising one or more wings extending from at least one of the distal portion and the proximal portion.

9. The system of claim 8, wherein at least one of the distal portion, the proximal portion, and the one or more wings is provided with a textured surface to resist sliding of the grasper receiving section from between jaws of the surgical instrument.

10. The system of claim 8, wherein the one or more wings are configured with an arcuate contour on an edge of at least one of a proximal and distal end of the one or more wings.

11. The system of claim 8, wherein the one or more wings are narrower proximally and extend wider distally.

12. The system of claim 1, wherein the grasper receiving section comprises a lumen, the lumen extending through the distal portion and the proximal portion, wherein the grasper receiving section comprises two or more co-extruded layers.

13. The system of claim 1, wherein the grasper receiving section comprises a lumen, the lumen extending through the distal portion and the proximal portion, wherein the grasper receiving section includes a stepdown configured to provide a wider lumen proximally and a narrower lumen distally.

14. A system for adapting a tubular surgical device for grasping by a surgical instrument, the system comprising:
a graspable component comprising:
a grasper receiving section comprised of a biocompatible material selected from polyurethanes, aliphatic or semialiphatic polyamides, polysulfone, silicone, polycarbonate, polyvinyl chloride, acrylonitrile butadiene styrene (ABS), acrylic, and block copolymers made up of rigid polyamide blocks and soft polyether blocks (PEBAX®),
the grasper receiving section formed from a unitary piece of material, the grasper receiving section comprising a distal portion comprising one or more diversion holes to provide an alternative fluid pathway during suction: and
a proximal portion including a male adaptor having a smaller outer diameter than the distal portion, wherein the male adaptor is configured to be disposed within a lumen of a tubular surgical device comprised of polyvinyl chloride, polyurethane, or silicone, the graspable component further comprising a portion molded over the adaptor to form an overmolded portion, and further comprising one or more wings positioned on the overmolded portion.

15. The system of claim 14, wherein the one or more wings are configured with an arcuate contour on an edge of at least one of a proximal and distal end of the one or more wings.

16. The system of claim 14, wherein the one or more wings are narrower proximally and extend wider distally.

* * * * *